United States Patent [19]

Ohno et al.

[11] Patent Number: 5,401,739
[45] Date of Patent: Mar. 28, 1995

[54] BENZOTHIADIAZINE DERIVATIVES

[75] Inventors: Tomoyasu Ohno; Shingo Yano, both of Hannou; Kosuke Fujiwara, Tokushima; Hirofusa Ajioka, Tokushima; Noriyuki Yamamoto, Tokushima; Shozo Yamada, Naruto; Makoto Kajitani, Hidaka, all of Japan

[73] Assignee: Taiho Pharmaceutical Co. Ltd., Tokyo, Japan

[21] Appl. No.: 142,307
[22] PCT Filed: May 22, 1992
[86] PCT No.: PCT/JP92/00672
  § 371 Date: Nov. 23, 1993
  § 102(e) Date: Nov. 23, 1993
[87] PCT Pub. No.: WO92/20666
  PCT Pub. Date: Nov. 26, 1992

[30] Foreign Application Priority Data

May 24, 1991 [JP] Japan .................. 3-149927

[51] Int. Cl.⁶ .................. A61K 31/54; C07D 285/24
[52] U.S. Cl. .................................. 514/223.2; 544/12
[58] Field of Search ................. 544/12; 514/223.2

[56] References Cited

U.S. PATENT DOCUMENTS 4,558,044 12/1985 King .................................. 514/222
4,590,192 5/1986 Fake et al. ....................... 514/231

FOREIGN PATENT DOCUMENTS 0172968 3/1986 European Pat. Off. .

Primary Examiner—John M. Ford
Attorney, Agent, or Firm—Nikaido, Marmelstein, Murray & Oram

[57] ABSTRACT

A benzothiadiazine derivative, hydrate thereof and acid addition salt thereof, the derivative being represented by the general formula (I)

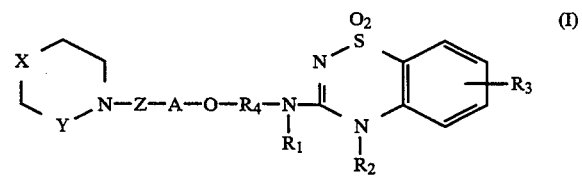

wherein X is methylene or a nitrogen atom substituted with a lower alkyl, Y and Z are each methylene or carbonyl, A is phenylene or phenylene substituted with methoxycarbonyl, $R_4$ is lower alkylene or lower alkenylene, $R_1$ is a hydrogen atom, acetoxyacetyl, cyclohexylmethyl or benzyl wherein the benzene ring may be substituted with lower alkoxyl, halogen atom, nitro, lower alkyl, methylenedioxy or hydroxyl, $R_2$ is lower alkyl or phenyl, and $R_3$ is a hydrogen atom, halogen atom or lower alkoxyl with the exception of the case where X, Y and Z are each methylene, A is unsubstituted phenylene, $R_4$ is lower alkylene and $R_1$ is a hydrogen atom; and a peptic ulcer treating agent containing as an effective component the above derivative, hydrate thereof or acid addition salt thereof.

8 Claims, No Drawings

BENZOTHIADIAZINE DERIVATIVES

TECHNICAL FIELD

The present invention relates to novel benzothiadiazine derivatives, hydrates thereof and acid addition salts thereof. The compounds of the present invention have activity to inhibit secretion of gastric acid and activity to protect the gastric mucosa and are useful for treating peptic ulcers.

BACKGROUND ART

Ulcers occurring in the stomach or duodenum are caused primarily by hypersecretion of gastric acid. Some drugs are known recently for inhibiting the secretion of gastric acid by blocking the activity of the histamine $H_2$ receptor. Several kinds of drugs of this class, such as cimetidine and famotidine, are commercially available at present. However, although these histamine $H_2$ receptor antagonists exhibit high curing effects, they have the problem of being very likely to permit subsequent recurrence, so that it has been attempted to use such antagonists in combination with an anti-ulcer drug having activity to protect the gastric mucosa. Accordingly, drugs for treating peptic ulcers should preferably have activity to inhibit gastric acid secretion and activity to protect the gastric mucosa, and it is strongly desired to develop drugs having both of these activities.

DISCLOSURE OF THE INVENTION

We have conducted intensive research in view of the foregoing problem of the background art and consequently found that novel benzothiadiazine derivatives represented by the general formula (I) given below, hydrates thereof and acid addition salts thereof have excellent activities to suppress gastric acid secretion and to protect the gastric mucosa and are useful as medicinals. Thus, the present invention has been accomplished.

More specifically, the present invention provides benzothiadiazine derivatives, hydrates thereof and acid addition salts thereof, the derivatives being represented by the general formula (I)

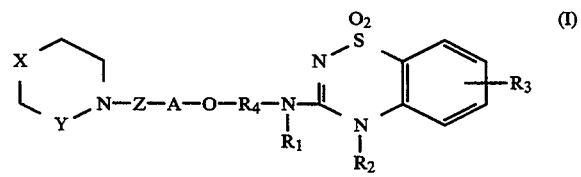

wherein X is methylene or a nitrogen atom substituted with a lower alkyl, Y and Z are each methylene or carbonyl, A is phenylene or phenylene substituted with methoxycarbonyl, $R_4$ is lower alkylene or lower alkenylene, $R_1$ is a hydrogen atom, acetoxyacetyl, cyclohexylmethyl or benzyl wherein the benzene ring may be substituted with lower alkoxyl, halogen atom, nitro, lower alkyl, methylenedioxy or hydroxyl, $R_2$ is lower alkyl or phenyl, and $R_3$ is a hydrogen atom, halogen atom or lower alkoxyl with the exception of the case where X, Y and Z are each methylene, A is unsubstituted phenylene, $R_4$ is lower alkylene and $R_1$ is a hydrogen atom.

The compounds of the present invention represented by the general formula (I) have excellent activities to inhibit gastric acid secretion and to protect the gastric mucosa and are effective for treating peptic ulcer.

Accordingly, the present invention provides a peptic ulcer treating agent containing a compound of the general formula (I), hydrate thereof or acid addition salt thereof in an effective amount and a pharmacological carrier.

The present invention further provides a method of treating peptic ulcer characterized by administering an effective amount of the compound of the general formula (I) to a patient.

With reference to the general formula (I), examples of lower alkyl groups as the substituent for the nitrogen atom represented by X, examples of lower alkyl groups represented by $R_2$ and examples of lower alkyl groups as the substituent on the benzene ring of $R_1$ are straight-chain or branched alkyl groups having 1 to 6 carbon atoms, such as methyl, ethyl, n-propyl, isopropyl, n-butyl, isobutyl, sec-butyl, tert-butyl, n-pentyl, isopentyl, n-hexyl and the like. Among these, methyl or n-butyl is preferred. Examples of lower alkoxyl groups represented by $R_3$ and examples of lower alkoxyl groups as the substituent on the benzene ring of $R_1$ are straight-chain or branched alkoxyl groups having 1 to 6 carbon atoms, such as methoxy, ethoxy, n-propoxy, isopropoxy, n-butoxy, isobutoxy, sec-butoxy, tert-butoxy, n-pentyloxy, isopentyloxy, n-hexyloxy and the like. Among these, methoxy is preferred. Examples of halogen atoms represented by $R_3$ and examples of halogen atoms as the substituent on the benzene ring of $R_1$ are fluorine atom, chlorine atom, bromine atom and iodine atom, among which chlorine atom is preferred.

Further with reference to the general formula (I), A is preferably phenylene, and more preferably meta-substituted phenylene. Examples of lower alkylene groups represented by $R_4$ are alkylene groups having 1 to 6 carbon atoms, such as methylene, ethylene, trimethylene, tetramethylene, pentamethylene, hexamethylene and the like. Among these, trimethylene is preferable. Examples of lower alkenylene groups are alkenylene groups having 2 to 6 carbon atoms, such as vinylene, propenylene, butenylene, pentenylene, hexenylene and the like. Although these groups can be cis- or trans-isomers, cis-butenylene group is preferable.

Examples of substituted benzyl groups represented by $R_1$, are those having 1 to 5, preferably 1 to 3, substituents.

The acid addition salts of benzothiadiazine derivatives of the invention are pharmacologically acceptable salts thereof such as salts with hydrochloric acid, sulfuric acid, phosphoric acid or like inorganic acid, or salts with maleic acid, succinic acid, malic acid, oxalic acid, fumaric acid or like organic acid.

Preferable among the compounds of the formula (I) are those wherein X, Y and Z are each methylene, A is phenylene, $R_4$ is trimethylene, $R_1$ is benzyl substituted with methoxy, $R_2$ is lower alkyl and $R_3$ is a hydrogen atom, or those wherein X, Y and Z are each methylene, A is phenylene, $R_4$ is butenylene, $R_1$ is a hydrogen atom, $R_2$ is lower alkyl and $R_3$ is a hydrogen atom. The most preferable compounds are those wherein X, Y and Z are each methylene, A is meta-substituted phenylene, $R_4$ is trimethylene, $R_1$ is methoxy-substituted benzyl, $R_2$ is methyl or n-butyl and $R_3$ is a hydrogen atom, or those wherein X, Y and Z are each methylene, A is meta-substituted phenylene, $R_4$ is cis-butenylene, $R_1$ is a hydrogen atom, $R_2$ is methyl or n-butyl and $R_3$ is a hydrogen atom.

The compound of the invention represented by the general formula (I) can be prepared, for example, by the process represented by the following reaction scheme (i).

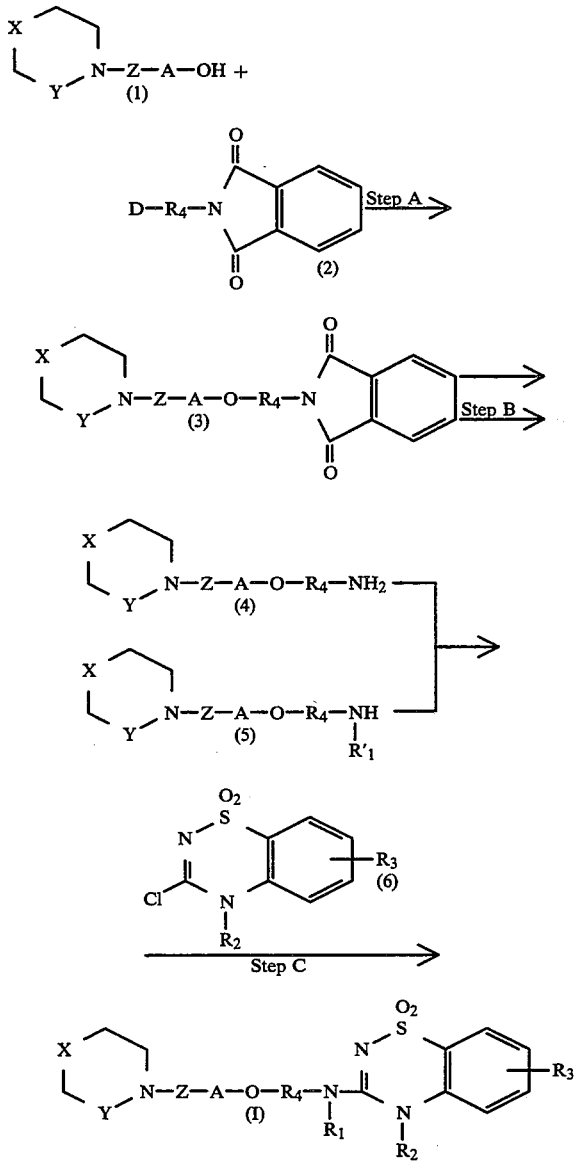

wherein D is a halogen atom, R'₁ is acetoxyacetyl, cyclohexylmethyl or benzyl wherein the benzene ring may be substituted with lower alkoxyl, halogen atom, nitro, lower alkyl, methylenedioxy or hydroxyl, and X, Y, Z, A, R₄, R₁, R₂ and R₃ are each as defined above.

Step A

According to the process disclosed in JP-A-115750/1981 and JP-A-178/1990, a compound represented by the general formula (1) is reacted with a known compound represented by the general formula (2) in a suitable solvent in the presence of a base to obtain a compound represented by the general formula (3). The solvent is not limited specifically insofar as the solvent does not participate in the reaction. Examples of solvents usable are dichloromethane, chloroform and like hydrocarbon halides, ethyl ether, tetrahydrofuran and like ethers, N,N-dimethylformamide, dimethyl sulfoxide and like aprotic polar solvents, etc. Examples of useful bases are pyridine, triethylamine and like organic amines, sodium carbonate, potassium hydroxide, sodium hydride and like inorganic bases. For the above reaction, it is desirable to use about 1 to about 3 moles of the compound of the formula (2) and about 1 to about 2 moles of the base per mole of the compound of the formula (1). The reaction temperature is 0° to 100° C., preferably 10° to 70° C. The reaction takes about 1 to about 24 hours for completion.

The compound of the formula (3) obtained by the above step is deprotected by hydrazine which is usually resorted to, whereby a compound of the general formula (4) can be obtained.

Step B

An acid chloride, aliphatic aldehyde compound or aromatic aldehyde compound is reacted with the amino compound of the formula (4) obtained in a suitable solvent to obtain a secondary amine of the general formula (5). For example, when R¹ is cyclohexylmethyl or substituted benzyl, the amino of the formula (5) is prepared by reacting the compound (4) with a corresponding aliphatic aldehyde or substituted benzaldehyde in a suitable solvent, and reacting a reducing agent with the resulting product. The solvent is not limited specifically insofar as it does not participate in the reaction. Examples of solvents usable are dichloromethane, chloroform and like hydrocarbon halides, ethyl ether, tetrahydrofuran and like ethers, benzene, toluene and like aromatic hydrocarbons, methanol, ethanol and like alcohols, etc. Examples of useful reducing agents are lithium aluminum hydride, sodium borohydride, etc. For the reaction, it is desired to use about 0.5 to about 5 moles, preferably about 2 moles, of the aliphatic or aromatic aldehyde compound and about 0.5 to about 2 moles, preferably about 1 mole, of the reducing agent per mole of the compound of the formula (4). The reaction temperature is 0° to 60° C., preferably 5° to 30° C. The reaction takes about 1 to about 24 hours for completion.

In the case where R₁ is acetoxyacetyl, the compound (4) is reacted with acetoxyacetyl chloride in a suitable solvent in the presence of a base, whereby the compound (5) is prepared. The solvent is not limited specifically insofar as it does not participate in the reaction. Examples of useful solvents are dichloromethane, chloroform and like hydrocarbon halides, ethyl ether, tetrahydrofuran and like ethers, benzene, toluene and like aromatic hydrocarbons, N,N-dimethylformamide, dimethyl sulfoxide and like aprotic polar solvents, etc. Examples of useful bases are pyridine, dimethylaminopyridine, triethylamine and like organic amines, sodium carbonate, potassium carbonate and like inorganic bases.

For the above reaction, about 1 to about 2 moles of acetoxyacetyl chloride and about 1 to about 2 moles of the base are used per mole of the compound of the formula (4). The reaction temperature is 0° to 100° C., preferably 5° to 40° C. The reaction takes about 1 to about 24 hours for completion.

Step C

The compound represented by the formula (4) or (5) is reacted with a 1,2,4-benzothiadiazine derivative represented by the formula (6) in a suitable solvent to obtain the compound of the present invention represented by the formula (I).

The solvent is not limited specifically insofar as it does not participate in the reaction. Examples of solvents usable are dichloromethane, chloroform and like hydrocarbon halides, ethyl ether, tetrahydrofuran and like ethers, benzene, toluene and like aromatic hydrocarbons, N,N-dimethylformamide, dimethyl sulfoxide and like aprotic polar solvents, etc. For the reaction, about 1 to about 3 moles of the compound of the formula (6) is used per mole of the compound of the formula (4) or (5). The reaction temperature is 0° to 80° C., preferably 10° to 40° C. The reaction takes about 1 to about 24 hours for completion.

Compounds of the invention can be prepared by another process. More specifically, the compound of the formula (I) wherein $R_1$ is acetoxyacetyl can be obtained by reacting a compound of the formula (4) with a compound of the formula (6) in a suitable solvent to prepare a secondary amine of the formula (I) wherein $R_1$ is a hydrogen atom, and reacting this compound with acetoxyacetyl chloride in the presence of a base. The reaction can be effected in the same manner as in the step B or C described.

The compound represented by the formula (1) to be used as a starting material according to the reaction scheme (i) can be prepared according to the following reaction schemes (ii) to (iv).

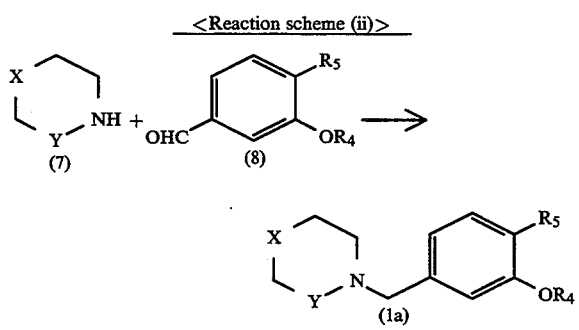

wherein $R_4$ is a hydrogen atom, methyl or protective group for phenolic hydroxyl, $R_5$ is a hydrogen atom or methoxycarbonyl, and X and Y are each the same as defined above.

The protective group $R_4$ for phenolic hydroxyl is, for example, lower alkoxycarbonyl or methoxymethyl.

A compound represented by the general formula (7) is reacted with a known aromatic aldehyde represented by the general formula (8) in a suitable solvent, and a suitable reducing agent is reacted with the resulting product, whereby a compound represented by the general formula (1a) is obtained. The solvent is not limited specifically insofar as it does not participate in the reaction. Examples of useful solvents are dichloromethane, chloroform and like hydrocarbon halides, ethyl ether, tetrahydrofuran and like ethers, benzene, toluene and like aromatic hydrocarbons, methanol, ethanol and like alcohols, etc. Examples of useful reducing agents are lithium aluminum hydride, sodium borohydride, etc. For the reaction, it is desired to use about 0.5 to about 5 moles, preferably about 2 moles, of the compound of the formula (8) and about 0.5 to about 2 moles, preferably about 1 mole, of the reducing agent per mole of the compound of the formula (7). The reaction temperature is 0° to 60° C., preferably 5° to 30° C. The reaction takes about 1 to about 24 hours for completion.

Alternatively, the compound represented by the formula (1a) is prepared according to the following reaction scheme (iii).

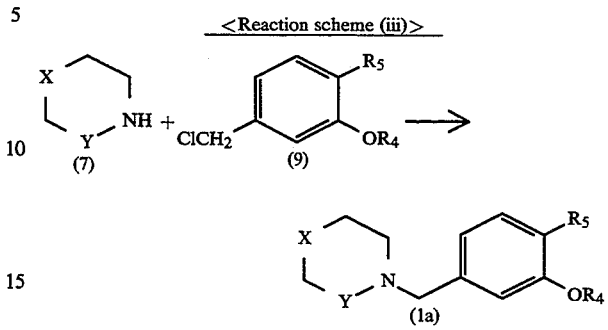

wherein X, Y, $R_4$ and $R_5$ are as defined above.

A compound of the formula (7) is reacted with a substituted benzyl chloride represented by the general formula (9) in a suitable solvent, whereby a compound of the formula (1a) is obtained. The solvent is not limited specifically insofar as it does not participate in the reaction. Examples of useful solvents are dichloromethane, chloroform and like hydrocarbon halides, ethyl ether, tetrahydrofuran and like ethers, benzene, toluene and like aromatic hydrocarbons, N,N-dimethylformamide, dimethyl sulfoxide and like aprotic polar solvents, etc. For the reaction, about 0.5 to about 2 moles, preferably about 1 mole, of the compound of the formula (9) is used per mole of the compound of the formula (7). The reaction temperature is 0° to 100° C., preferably 50° to 70° C. The reaction takes about 1 to about 24 hours for completion.

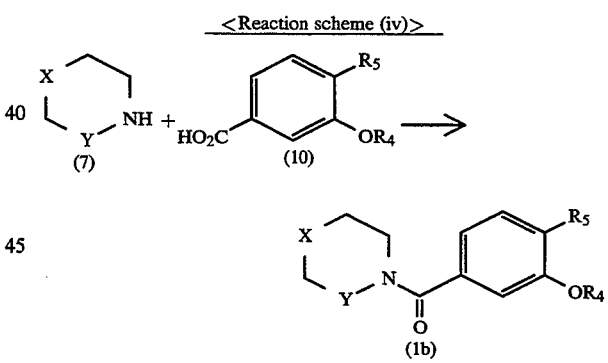

wherein X, Y, $R_4$ and $R_5$ are as defined above.

A compound of the formula (7) is reacted with a substituted aromatic carboxylic acid represented by the general formula (10) in a suitable solvent using a condensing agent in the presence of a base, whereby a compound of the general formula (1b) is obtained. The solvent is not limited specifically insofar as it does not participate in the reaction. Examples of solvents usable are dichloromethane, chloroform and like hydrocarbon halides, ethyl ether, tetrahydrofuran and like ethers, benzene, toluene and like aromatic hydrocarbons, N,N-dimethylformamide, dimethyl sulfoxide and like aprotic polar solvents, etc. Examples of useful bases are pyridine, dimethylaminopyridine, triethylamine and like organic amines, sodium carbonate, potassium carbonate and like inorganic bases. Examples of useful condensing agents are N,N'-dicyclohexylcarbodiimide, those of the phosphoric acid type which are usually used, such as diethyl cyanophosphate and diphenylphosphoric acid azide, etc. For the reaction are used about 1 to about 2 moles of the compound of the formula (10), about 1 to about 2 moles of the base and about 1 to about 2 moles of the condensing agent per mole of the compound of the formula (7). The reaction temperature is 0° to 100° C., preferably 5° to 40° C. The reaction takes about 1 to about 24 hours for completion.

In the case where the compound (1a) or (1b) prepared according to the foregoing scheme (ii), (iii) or (iv) has a protective group as $R_4$, the protective group is removed by the conventional method to obtain a compound (1). The solvent to be used is not limited specifically insofar as it does not participate in the reaction. For example, water, acetic acid or like polar solvent is preferred. For example, when $R_4$ is methyl, about 1 to about 10 moles, preferably about 2 to about 5 moles, of 47% hydrobromic acid is used per mole of the compound (1a) or (1b). The reaction temperature is 30° to 100° C., preferably 50° to 90° C. The reaction takes about 1 to about 24 hours for completion.

An inorganic or organic acid is added to the compound of the formula (I) as dissolved in a suitable solvent, whereby a corresponding inorganic or organic salt is obtained. The solvent is not limited specifically insofar as it does not participate in the reaction. Examples of useful solvents are dichloromethane, chloroform and like hydrocarbon halides, ethyl ether, tetrahydrofuran and like ethers, methanol, ethanol and like alcohols, ethyl acetate and like esters, etc. For the formation of salt, the desired inorganic or organic acid is added to the compound of the formula (I) with ice cooling and stirring in an amount of about 1 to about 3 moles, preferably about 1.5 moles, of the acid per mole of the compound (I), followed by crystallization from ethyl ether or like solvent of low polarity, whereby the desired salt is prepared.

The compound (6) is a known compound and can be prepared, for example, by the process disclosed in SYNTHESIS, 1986, 864.

The compounds obtained according to the foregoing reaction schemes can be isolated and purified by methods which are generally used in the art, such as concentration, filtration, recrystallization and various chromatographic procedures.

For use as medicaments, the compound of the present invention can be administered in various forms in comformity with the preventive or treating purpose contemplated. The compound may be given, for example, in the form of any or oral preparation, injection, suppository and the like. Such preparations can be produced by conventional pharmaceutical methods known in the art.

Solid preparations for oral administration can be produced in a usual manner by adding to the present compound an excipient, and when required, a binder, disintegrator, lubricant, coloring agent, corrigent, flavor and the like, and making the mixture into tablets, coated tablets, granules, powders or an encapsulated preparation. Such additives are those generally used in the art. Examples of useful excipients are lactose, sucrose, sodium chloride, glucose, starch, calcium carbonate, kaolin, microcrystalline cellulose, silicic acid and the like. Examples of useful binders are water, ethanol, propanol, syrup, glucose solution, starch solution, gelatin solution, carboxymethyl cellulose, hydroxypropyl cellulose, hydroxypropyl starch, methyl cellulose, ethyl cellulose, shellac, calcium phosphate, polyvinylpyrrolidone and the like. Examples of useful disintegrators are dried starch, sodium alginate, agar powder, sodium hydrogencarbonate, calcium carbonate, sodium laurylsulfate, stearic acid monoglyceride, lactose and the like. Examples of useful lubricants are purified talc, stearic acid salts, borax, polyethylene glycol and the like. Examples of useful corrigents are sucrose, bitter orange peel, citric acid, tartaric acid and the like.

Liquid preparations for oral administration can be produced in a usual manner by adding a corrigent, buffer, stabilizer, flavor and the like to the present compound, and making the mixture into a liquid oral preparation, syrup, elixir or the like. Examples of useful corrigents are those exemplified above. Examples of useful buffers are sodium citrate and the like. Examples of useful stabilizers are tragacanth, gum arabic, gelatin and the like.

Injections can be produced in a usual manner by adding a pH adjusting agent, buffer, stabilizer, isotonic agent, local anesthetic and the like to the present compound, and formulating the mixture into a preparation for subcutaneous, intramuscular or intravenous injection. Examples of useful pH adjusting agents and buffers are sodium citrate, sodium acetate, sodium phosphate and the like. Examples of useful local anesthetics are procaine hydrochloride, lidocaine hydrochloride and the like.

Suppositories can be prepared by adding to the present compound a pharmaceutical carrier known in the art, such as polyethylene glycol, lanolin, cacao fat, fatty acid triglyceride or the like, along with Tween (registered trademark) or like surfactant and the like when desired, and treating the mixture in the usual manner.

Although the amount of the present compound to be contained in the unit form of each preparation varies with the symptoms of the patient, the type of preparation, etc., the amount is generally preferably about 1 to about 1000 mg for oral administration, about 0.1 to about 500 mg for injection or about 5 to 1000 mg for suppositories, per unit of the preparation. The dosage per day of the compound to be given in the form of such a preparation can not be determined specifically but varies with the symptoms, weight, age, sex, etc. of the patient. However, it is given usually at a dose of about 0.1 to about 5000 mg, preferably 1 to 1000 mg, per day for adults, preferably once or two to four divided doses.

BEST MODE FOR CARRYING OUT THE INVENTION

The present invention will be described below in greater detail with reference to examples and reference examples. In the Table, Me, Et, Bu, Ph and Ac stand for methyl, ethyl, butyl, phenyl and acetyl respectively. MS means mass spectrum analysis.

REFERENCE EXAMPLE 1

Synthesis of 3-(1-piperidinomethyl)phenol

In 800 ml of ethanol was dissolved 122 g of 3-hydroxybenzaldehyde and thereto was gradually added 210 g of piperidine. To the mixture was added 38 g of sodium borohydride under cooling with ice and the mixture was stirred for 8 hours at room temperature. The resulting mixture was concentrated at a reduced pressure. To a residue were added ice-cold water and hydrochloric acid to render a solution acidic. The solution was washed with diethyl ether. An aqueous layer was made alkaline with addition of sodium carbonate and then extracted with ethyl acetate. After removing the solvent, 106 g (yield 55%) of 3-(1-piperidinomethyl)phenol was obtained in the form of white crystal.

REFERENCE EXAMPLE 2

Synthesis of 1-(3-hydroxybenzyl)-2-piperidone

In 6 ml of N,N-dimethylformamide was suspended 0.8 g of 60% sodium hydride and thereto was added dropwise a solution of 1.98 g of 2-piperidone in 8 ml of N,N-dimethylformamide under a stream of argon and with ice cooling. Then, to the mixture was added dropwise a solution of 2.82 g of 3-methoxybenzyl chloride in 8 ml of N,N-dimethylformamide at room temperature. The mixture was stirred at 65° C. for 8 hours. After cooling, to the reaction mixture were added ice-cold water and the mixture was extracted with diethyl ether. The extract was purified by a silica gel column chromatography (chloroform:methanol=20:1) to give 4.3 g of 1-(3-methoxybenzyl)-2-piperidone. This compound was heated in 10 ml of 47% hydrobromic acid for 12 hours. The mixture was made alkaline with addition of sodium carbonate and extracted with chloroform. After removing the solvent at a reduced pressure, 2.3 g (yield 57%) of 1-(3-hydroxybenzyl)-2-piperidone was obtained.

REFERENCE EXAMPLE 3

Synthesis of 3-(1-piperidinocarbonyl)phenol

To a solution of 2.2 ml of piperidine in 30 ml of dichloromethane were added 3 g of 3-hydroxybenzoic acid, 0.27 g of dimethylaminopyridine and 4.5 g of N,N'-dicyclohexylcarbodiimide with ice cooling and the mixture was stirred for 8 hours. The reaction mixture was extracted with water-ethyl acetate and the solvent was removed from an organic layer. The residue was purified by a silica gel column chromatography (chloroform:methanol=50:1) to give 3.8 g (yield 85%) of 3-(1-piperidinocarbonyl)phenol in the form of white crystal.

REFERENCE EXAMPLE 4

To a solution of 5.2 g of chlorosulfonylisocyanate in 45 ml of nitromethane was gradually added dropwise a solution of N-methylaniline in nitromethane. Thereto was added 5.1 g of aluminum chloride and the mixture was heated with reflux for 30 minutes. After cooling, the mixture was poured into ice-cold water and precipitated crystals were collected with filtration. The crystals were recrystallized from ethanol to give 3.1 g (yield 48%) of 2H-4-methyl-1,2,4-benzothiaziadine-3-one-1,1-dioxide in the form of white crystal.

In 3 ml of 1,2-dichlorobenzene was suspended 500 mg of 2H-4-methyl-1,2,4-benzothiaziadine-3-one-1,1-dioxide and thereto was added 540 mg of phosphorus pentachloride. The mixture was stirred at 170° C. for 1.5 hours. The solvent was removed at 85° C. under reduced pressure to give 480 mg (yield 88%) of 3-chloro-4-methyl-1,2,4-benzothiaziadine-1,1-dioxide.

EXAMPLE 1

Preparation of 3-[N-[3-[3-(piperidinomethyl)phenoxy]propyl]-4'-methoxybenzylamino]-4-methyl-1,2,4-benzothiadiazine-1,1-dioxide (compound 1)

(i) In an argon stream, 2.2 g of 60% sodium hydride was suspended in 20 ml of N,N-dimethylformamide. The suspension was added dropwise to a solution of 9.6 g of the 3-(1-piperidinomethyl)phenol obtained in Reference Example 1 in 30 ml of N,N-dimethylformamide, followed by stirring at room temperature for 30 minutes. Next, a solution of 14.7 g of N-(3-bromopropyl)phthalimide in 50 ml of N,N-dimethylformamide was added dropwise to the mixture, and the resulting mixture was stirred at 65° C. for 8 hours. After cooling the mixture, a mixture of diethyl ether and water (1:1) was added thereto for extraction, and the organic layer was concentrated under reduced pressure. To the concentrate was added 6N hydrochloric acid for extraction into the aqueous layer, which was then made alkaline with potassium hydroxide, followed by extraction with diethyl ether. The organic layer was dried over magnesium sulfate and distilled under reduced pressure to remove the solvent, giving 16.3 g of transparent oily N-[3-[3-(piperidinomethyl)-phenoxy]propyl]phthalimide (yield 86%).

(ii) To a solution of 16.3 g of the N-[3-[3-(piperidinomethyl)phenoxy]propyl]phthalimide in 150 ml of methanol was added 2.3 g of hydrazine monohydrate, and the mixture was heated at 70° C. for 4 hours. The mixture was cooled, then the solvent was distilled off, 30 ml of 6N hydrochloric acid was added to the residue, and the mixture was heated at 60° C. for 15 minutes. The resulting mixture was cooled, the insolubles were then filtered off, the solution was made alkaline with potassium hydroxide and subjected to extraction with a mixture of ethyl acetate and diethyl ether (1:1), and the organic layer was dried over magnesium sulfate and thereafter distilled to remove the solvent, giving 8.3 g of pale yellow oily 3-[3-(1-piperidinomethyl)phenoxy]propylamine (yield 78%).

(iii) A solution of 16.9 g of 3-[3-(1-piperidinomethyl)-phenoxy]propylamine in 25 ml of ethanol was added dropwise to a solution of 9.3 g of p-anisaldehyde in 50 ml of ethanol. The mixture was stirred at room temperature for 20 minutes, 2.9 g of sodium borohydride was then added to the mixture with ice cooling, and the resulting mixture was stirred at room temperature for 8 hours and thereafter distilled under reduced pressure to remove the solvent. With addition of ice-cold water first and then 6N hydrochloric acid, the residue was made into an acid solution, which was then washed with ethyl acetate. The aqueous layer was made alkaline with potassium hydroxide and subjected to extraction with ethyl acetate. The organic layer was dried over magnesium sulfate and thereafter distilled under reduced pressure to remove the solvent, affording 20.3 g of N-[3-[3-(piperidinomethyl)phenoxy]propyl]-4'-methoxybenzylamine (yield 80%).

(iv) To a solution of 320 mg of the N-[3-[3-(piperidinomethyl)phenoxy]propyl]-4'-methoxybenzylamine in 5 ml of chloroform was added 200 mg of the 3-chloro-4-methyl-1,2,4-benzothiadiazine-1,1-dioxide obtained in Reference Example 4, and the mixture was stirred at room temperature for 8 hours. The solvent was distilled off from the mixture, and the residue was treated by silica gel column chromatography using chloroform:methanol (20:1) to isolate purified 3-[N-[3-[3-(piperidinomethyl)-phenoxy]propyl]-4'-methoxybenzylamino]-4-methyl-1,2,4-benzothiadiazine-1,1-dioxide in an amount of 480 mg (yield 98%). The product was made into an ethanol solution, to which a solution of 110 mg of dihydrate of oxalic acid in ethanol was added dropwise with ice cooling, followed by addition of diethyl ether for conversion to an oxalic acid salt. Thus, 400 mg of a compound 1 was obtained in the form of white crystals as listed in Table 1 (yield 68%). M.p.: 65°~70° C. (dec.)

EXAMPLE 2

One gram of the compound obtained in Example 1, (iv), i.e., 3-[N-[3-[3-(piperidinomethyl)phenoxy]-propyl]-4'-methoxybenzylamino]-4-methyl-1,2,4-benzothiadiazine-1,1-dioxide, was dissolved in 10 ml of ethyl acetate. To the solution was added dropwise 1 ml of 4N hydrochloric acid/ethyl acetate with ice cooling, followed by dropwise addition of 5 ml of n-hexane to give a hydrochloride, i.e., 1.05 g of a compound 2 in the form of white crystals as listed in Table 1(yield 98%). M.p.: 94°~99° C.

EXAMPLE 3

Compounds 3~9 and 11~14 listed in Table 1 were prepared by repeating the procedure of Example 1 with use of corresponding substituted benzaldehydes in place of p-anisaldehyde used in Example 1, (iii).

EXAMPLE 4

A 0.8 g quantity of 3-chloro-4-ethyl-1,2,4-benzothiadiazine-1,1-dioxide in the form of white crystals prepared in the same manner as in Reference Example 4 with the exception of using N-ethylaniline in place of N-methylaniline was added to a solution of 1.2 g of the N-[3-[3-(piperidinomethyl)phenoxy]propyl]-4'-methoxybenzylamine obtained in Example 1, (iii) in 12 ml of chloroform, and the mixture was stirred at room temperature for 8 hours. The reaction mixture was purified in the same manner as in Example 1, giving 1.67 g of 3-[N-[3-[3-(piperidinomethyl)phenoxy]-propyl]-4'-methoxybenzylamino]-4-ethyl-1,2,4-benzothiadiazine-1,1-dioxide (yield 88%). This compound was converted to an oxalic acid salt in the same manner as in Example 1 to obtain 1.81 g of a compound 15 in the form of white crystals as listed in Table 1 (yield 92%). M.p.: 85°~90° C.

EXAMPLE 5

Compounds 16~20 listed in Table 1 were prepared in the same manner as in Examples 1 and 4 with the exception of using corresponding N-substituted anilines in place of N-methylaniline used in Reference Example 4.

EXAMPLE 6

3-[3-(4-Methyl-1-piperazinylmethyl)phenoxy]-propylamine was obtained by repeating the procedures of Reference Example 1 and Example 1 using N-methylpiperazine instead of piperidine used in Reference Example 1. This compound (1.0 g) was dissolved in 30 ml of chloroform, 0.88 g of the 3-chloro-4-methyl-1,2,4-benzothiadiazine-1,1-dioxide obtained in Reference Example 4 was added to the solution, and the mixture was stirred at room temperature for 8 hours. After removing the solvent from the mixture by distillation, the residue was purified by silica gel column chromatography (chloroform:methanol=20:1). The purified product was then dissolved in ethyl acetate, and a solution of 4N hydrochloric acid and ethyl acetate was added dropwise to the soltuion, giving 1.72 g of a white crystalline hydrochloride, i.e., 3-[N-[3-[3-(4-methyl-1-piperazinylmethyl)phenoxy]propyl]amino]-4-methyl-1,2,4-benzothiadiazine-1,1-dioxide (compound 24, yield 92%). M.p.: 218°~223° C. (dec.)

EXAMPLE 7

(i) In an argon stream with ice cooling, a solution of 2.3 g of the 1-(3-hydroxybenzyl)-2-piperidone obtained in Reference Example 2 in 10 ml of N,N-dimethylformamide was added dropwise to a soltuion of 0.44 g of 60% sodium hydride in 5 ml of N,N-dimethylformamide. Subsequently, a solution of 2.8 g of N-(3-bromopropyl)phthalimide in 10 ml of N,N-dimethylformamide was added dropwise to the mixture at room temperature, followed by stirring at 65° C. for 8 hours. The resulting mixture was cooled, ice-cold water was thereafter added thereto, the mixture was subjected to extraction with diethyl ether, 6N hydrochloric acid was then added to the organic layer for extraction into the aqueous layer, and the aqueous layer was made alkaline with sodium hydroxide, followed by extraction with diethyl ether again. The organic layer was dried over magnesium sulfate and thereafter distilled to remove the solvent, giving N-[3-[3-(2-oxopiperidinomethyl)-phenoxy]propyl]phthalimide. This compound was hydrolyzed with hydrazine in the same manner as in Example 1, (ii) to afford 1.4 g of 3-[3-(2-oxopiperidinomethyl)phenoxy]propylamine (yield 51%).

(ii) The 3-[3-(2-oxopiperidinomethyl)phenoxy]-propylamine (1.4 g) was dissolved in 10 ml of chloroform. To the solution was slowly added 0.7 g of the 3-chloro-4-methyl-1,2,4-benzothiadiazine-1,1-dioxide obtained in Reference Example 4, and the mixture was stirred at room temperature for 8 hours. The solvent was then removed from the mixture by distillation, and the residue was purified by silica gel column chromatography (chloroform:methanol=30:1), giving 1.1 g of white crystalline 3-(N-[3-[3-(2-oxopiperidinomethyl)-phenoxy]-propyl]amino]-4-methyl-1,2,4-benzothiadiazine-1,1-dioxide (compound 10, yield 83%). M.p.: 137°~138° C.

EXAMPLE 8

In 7 ml of chloroform was dissolved 1 g of 3-[3-(1-piperidinocarbonyl)phenoxy]propylamine which was prepared by the same procedure as in Example 1, (i) with the exception of using the 3-(1-piperidinocarbonyl)phenol obtained in Reference Example 3 instead of 3-(1-piperidinomethyl)phenol. The 3-chloro-4-methyl-1,2,4-benzothiadiazine-1,1-dioxide (0.88 g) obtained in Reference Example 4 was added to the solution, followed by the same procedure as in Example 1 to obtain 0.98 g of 3-[N-[3-[3-(1-piperidinocarbonyl)-phenoxy]propyl]amino]-4-methyl-1,2,4-benzothiadiazine-1,1-dioxide (compound 26, yield 56%). M.p.: 80°~82° C.

EXAMPLE 9

(i) To a solution of 10 g of 1,4-dichloro(trans) 2-butene in 100 ml of N,N-dimethylformamide was added 16.5 g of phthalimide potassium with ice cooling. The mixture was stirred at room temperature for 8 hours, the mixture was subjected to extraction with water-ethyl acetate, and the organic layer was distilled to remove the solvent. The residue was then purified by silica gel column chromatography (n-hexane:ethyl acetate=3:1), giving 9.6 g of N-[4-chloro(trans) 2-butenyl]phthalimide (yield 51%).

(ii) In the same manner as in Example 1, the N-[4-chloro(trans) 2-butenyl]phthalimide was reacted with 3-(1-piperidinomethyl)phenol, followed by hydrolysis with hydrazine to obtain 1.56 g of 4-[3-(1-piperidinomethyl)phenoxy]-(trans) 2-butenylamine. To a solution of 1 g of this amine compound in 30 ml of chloroform was added 0.9 g of the 3-chloro-4-methyl-1,2,4-benzothiadiazine-1,1-dioxide, followed by the same treatment as in Example 1 to obtain 1.57 g of white crystalline 3-[N-[4-[3-(1-piperidinomethyl)phenoxy]-(trans) 2-butenyl]amino]-4-methyl-1,2,4-benzothiadiazine-1,1-dioxide (compound 23, yield 90% ). M.p. 116°~120° C.

EXAMPLE 10

The same procedure as above was repeated using 1,4-dichloro-(cis) 2-butene instead of the 1,4-dichloro-(trans) 2-butene used in Example 9 to obtain white crystalline 3-[N-[4-[3-(piperidinomethyl)phenoxy]-(cis) 2-butenyl]amino]-4-methyl-1,2,4-benzothiadiazine-1,1-dioxide (compound 22) in a yield of 64%. M.p.: 138°~142° C.

EXAMPLE 11

The 3-chloro-4-methyl-1,2,4-benzothiadiazine-1,1-dioxide obtained in Reference Example 4 was reacted with 3-[3-(piperidinomethyl)phenoxy]propylamine in the same manner as in Example 1 to obtain 3-[N-]3-[3-(piperidinomethyl)phenoxy]-propyl]amino)-4-methyl-1,2,4-benzothiadiazine-1,1-dioxide. In an argon stream with ice cooling, 0.18 g of 60% sodium hydride was added to a solution of 1.78 g of this dioxide in 10 ml of N,N-dimethylformamide. To the mixture was added dropwise 0.6 g of acetoxyacetyl chloride, and the resulting mixture was stirred at room temperature for 12 hours. Ice-cold water was added to the reaction mixture, and the mixture was made alkaline with sodium hydroxide and subjected to extraction with ethyl acetate, followed by distillation to remove the solvent. The residue was purified by silica gel column chromatography using chloroform:methanol (10:1) to isolate 0.33 g of 3-[N-[3-[3-(piperidinomethyl)phenoxy]-propyl]acetoxyacetylamino]-4-methyl-1,2,4-benzothiadiazine-1,1-dioxide (yield 15% ). The oily product obtained was converted to an oxalic acid salt in the same manner as in Example 1 to obtain 0.28 g of a compound 21 listed in Table 1 (yield 71% ). M.p.: 86°~89° C.

EXAMPLE 12

The same procedure as in Example 9 was repeated using 3-(4-methyl-1-piperadinylmethyl)phenol instead of 3-(1-piperidinomethyl)phenol and 1,4-dichloro-(cis) 2-butene instead of 1,4-dichloro-(trans) 2-butene to obtain 3-[N-[4-[3-(4-methyl-1-piperadinylmethyl)phenoxy]-(cis) 2-butenyl]amino]-4-methyl-1,2,4-benzothiadiazine-1,1-dioxide. The product was made into an ethyl acetate solution, to which a solution of 4N hydrochloric acid and ethyl acetate was added dropwise with ice cooling for convertion to a hydrochloride. Thus, a compound 25 listed in Table 1 was obtained in a yield of 25%.

$^1$H-NMR(CDCl$_3$) δ ppm: 2.62 (3H, s), 2.84 (4H, brs), 2.99 (4H, brs), 3.56 (2H, s), 3.62 (3H, s), 4.14 (2H, brs), 4.72 (2H, d), 5.26 (2H, brs), 5.78 (2H, brs), 6.60~7.92 (8H, m)

EXAMPLE 13

3-[2-Carboxymethyl-5-(piperidinomethyl)phenoxy]-propylamine was prepared by the same procedures as in Reference Example 1 and Example 1 using 3-hydroxy-4-carboxymethylbenzaldehyde in place of the 3-hydroxybenzaldehyde used in Reference Example 1. This propylamine was reacted with the 3-chloro-4-methyl-1,2,4-benzothiadiazine-1,1-dioxide obtained in Reference Example 4 in the same manner as in Example 1. The reaction mixture was purified by silica gel column chromatography using chloroform:methanol (20:1) to isolate 3-[N-[3-[2-carboxymethyl-5-(piperidinomethyl)phenoxypropyl]-N-(4-methoxybenzyl)]amino]-4-methyl-1,2,4-benzothiadiazine-1,1-dioxide in a yield of 24%. The product was dissolved in ethyl acetate, and a solution of 4N hydrochloric acid and ethyl acetate was added dropwise to the solution with ice cooling to obtain a white crystalline hydrochloride. Thus, a compound 27 listed in Table 1 was prepared in a yield of 75%. M.p.: 93°~97° C.

EXAMPLE 14

The procedure of Example 9 was repeated using 1,4-dichloro-(cis) 2-butene in place of 1,4-dichloro-(trans) 2-butene and 3-chloro-4-n-butyl-1,2,4-benzothiadiazine-1,1-dioxide in place of 3-chloro-4-methyl-1,2,4-benzothiadiazine-1,1-dioxide, followed by crystallization to obtain a hydrochlride, i.e., white crystalline 3-[N-[4-[3-(piperidinomethyl)phenoxy]-(cis) 2-butenyl]amino]-4-methyl-2,4-benzothiadiazine-1,1-dioxide (compound 28) in a yield 60%.

$^1$H-NMR (CDCl$_3$) δ ppm: 0.95 (3H, t, J=7 Hz), 1.40~2.03 (10H, m), 2.86~3.04 (4H, m), 3.98~4.08 (2H, m), 4.01 (2H, s), 4.16~4.22 (2H, m), 4.88 (2H, m), 5.67~5.73 (1H, m), 5.84~5.92 (1H, m), 6.92~7.94(8H, m)

EXAMPLE 15

The procedure of Example 9 was repeated using 1,4-dichloro-(cis) 2-butene in place of 1,4-dichloro-(trans) 2-butene and 3-chloro-4-methyl-6-methoxy-1,2,4-benzothiadiazine-1,1-dioxide in place of 3-chloro-4-methyl-1,2,4-benzothiadiazine-1,1-dioxide, followed by crystallization to obtain a hydrochloride, i.e., white crystalline 3-[N-[4-[3-(piperidinomethyl)phenoxy]-(cis) 2-butenyl]amino]-4-methyl-6-methoxy-1,2,4-benzothiadiazine-1,1-dioxide (compound 29) in a yield of 65%.

$^1$H-NMR(CDCl$_3$) δ ppm: 1.55~1.83(6H, m), 2.68~2.82 (5H, m), 3.52 (3H, s), 3.76~3.82(2H, m), 3.84 (3H, s), 4.13~4.16 (2H, m), 4.76~4.79(2H, m), 5.71~5.78(1H, m), 5.82~5.92(1H, m), 6.85~7.42(7H, m)

TABLE 1

| Compound No. | Formula | MP (°C.) MS | Elementary Analysis Calcd Found |
|---|---|---|---|
| 1 | (structure) (CO₂H)₂.2H₂O MeO | 65–70 (dec.) MS 562 (M+) | $C_{31}H_{38}N_4O_4S.(CO_2H)_2.2H_2O$<br>C    H    N<br>57.54  6.44  8.13<br>57.81  6.37  7.81 |
| 2 | (structure) HCl.2H₂O MeO | 94–99 MS 562 (M+) | $C_{31}H_{38}N_4O_4S.HCl.2H_2O$<br>C    H    N<br>58.62  6.82  8.82<br>58.85  6.66  8.67 |
| 3 | (structure) (CO₂H)₂.H₂O | 108–111 MS 532 (M+) | $C_{30}H_{36}N_4O_3S.(CO_2H)_2.H_2O$<br>C    H    N<br>59.98  6.29  8.74<br>60.30  6.36  8.59 |
| 4 | (structure) (CO₂H)₂.3/2H₂O Cl | 93.5–96.5 MS 566 (M+) | $C_{30}H_{35}N_4O_3SCl.(CO_2H)_2.3/2H_2O$<br>C    H    N<br>56.18  5.89  8.19<br>56.34  5.74  8.13 |

TABLE 1-continued

| Compound No. | Formula | MP (°C.) MS | Elementary Analysis Calcd Found |
|---|---|---|---|
| 5 | [structure with piperidine, benzyl, propoxy-phenyl, sulfonyl-phenyl, N-Me, and p-NO2 benzyl] (CO2H)2·1/2H2O | 99–103 (dec.) MS 578 (M + 1) | C30H35N5O5S·(CO2H)2·1/2H2O<br>C  H  N<br>Calcd 56.79 5.66 10.35<br>Found 56.82 5.85 10.03 |
| 6 | [structure with p-Me benzyl] (CO2H)2·H2O | 80–82 MS 547 (M + 1) | C31H38N4O3S·(CO2H)2·H2O<br>C  H  N<br>60.53 6.47 8.56<br>60.67 6.42 8.31 |
| 7 | [structure with p-MeO benzyl] (CO2H)2·2H2O | 85–88 MS 563 (M+) | C31H38N4O4S·(CO2H)2·2H2O<br>C  H  N<br>57.54 6.44 8.13<br>57.70 6.23 7.92 |
| 8 | [structure with o-OMe benzyl] (CO2H)2·H2O | 80–83 MS 563 (M + 1) | C31H38N4O4S·(CO2H)2·H2O<br>C  H  N<br>59.09 6.31 8.35<br>59.09 6.29 8.36 |

TABLE 1-continued

| Compound No. | Formula | MP (°C.) MS | Elementary Analysis Calcd / Found |
|---|---|---|---|
| 9 | (structure with O$_2$S-phenyl, N-Me, N-CH$_2$-piperidine, propyl-O-phenyl-CH$_2$-N-piperidine, and dimethoxybenzyl group) · (CO$_2$H)$_2$·5/2H$_2$O | 83–87<br>MS 623 (M + 1) | C$_{33}$H$_{42}$N$_4$O$_6$S·(CO$_2$H)$_2$·5/2H$_2$O<br>C  H  N<br>55.47  6.52  7.39<br>55.67  6.24  7.33 |
| 10 | (structure with O$_2$S-phenyl, N-Me, NH, propyl-O-phenyl-CH$_2$-N-piperidinone) · 3/4H$_2$O | 137–138<br>MS 457 (M + 1) | C$_{23}$H$_{28}$N$_4$O$_4$S·3/4H$_2$O<br>C  H  N<br>58.77  6.33  11.92<br>58.84  6.51  11.95 |
| 11 | (structure with O$_2$S-phenyl, N-Me, N-CH$_2$-piperidine, propyl-O-phenyl-CH$_2$-N-piperidine, methylenedioxybenzyl) · (CO$_2$H)$_2$·2H$_2$O | 96–98<br>MS 577 (M + 1) | C$_{31}$H$_{36}$N$_4$O$_5$S·(CO$_2$H)$_2$·2H$_2$O<br>C  H  N<br>56.40  6.02  7.97<br>56.69  5.85  7.85 |
| 12 | (structure with O$_2$S-phenyl, N-Me, N-CH$_2$-piperidine, propyl-O-phenyl-CH$_2$-N-piperidine, hydroxyphenyl) · (CO$_2$H)$_2$·1/3H$_2$O | 102–106<br>MS 548 (M+) | C$_{30}$H$_{36}$N$_4$O$_4$S·(CO$_2$H)$_2$·1/3H$_2$O<br>C  H  N<br>59.61  6.04  8.69<br>59.58  6.27  8.53 |

TABLE 1-continued
| Compound No. | Formula | MP (°C.) MS | Elementary Analysis Calcd Found |
|---|---|---|---|
| 13 | 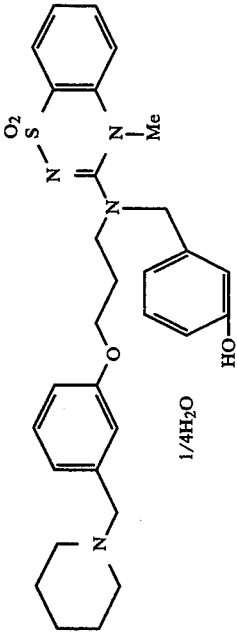 1/4H$_2$O | 78.5–79.5 MS 547 (M − 1) | C$_{30}$H$_{36}$N$_4$O$_4$S·1/4H$_2$O<br>C  H  N<br>65.14  6.65  10.13<br>65.22  6.91  9.91 |
| 14 | 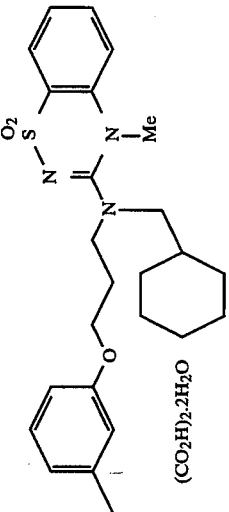 (CO$_2$H)$_2$·2H$_2$O | 83.5–85.5 MS 539 (M + 1) | C$_{30}$H$_{42}$N$_4$O$_3$S·(CO$_2$H)$_2$·2H$_2$O<br>C  H  N<br>57.81  7.28  8.43<br>57.70  7.01  8.18 |
| 15 | 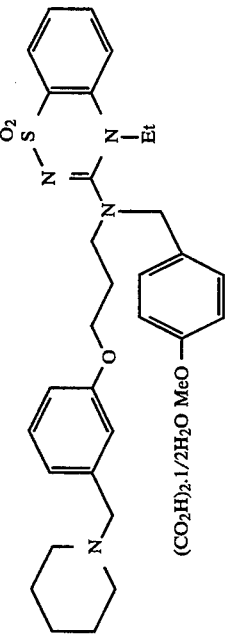 (CO$_2$H)$_2$·1/2H$_2$O MeO | 85–90 MS 577 (M + 1) | C$_{32}$H$_{40}$N$_4$O$_4$S·(CO$_2$H)$_2$·1/2H$_2$O<br>C  H  N<br>60.43  6.41  8.29<br>60.15  6.52  8.00 |
| 16 | 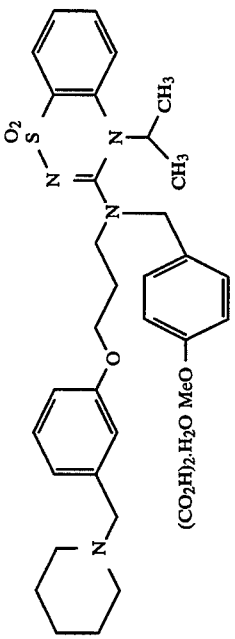 (CO$_2$H)$_2$·H$_2$O MeO | 81–86 MS 591 (M + 1) | C$_{33}$H$_{42}$N$_4$O$_4$S·(CO$_2$H)$_2$·H$_2$O<br>C  H  N<br>60.15  6.63  8.02<br>60.38  6.63  7.76 |

TABLE 1-continued

| Compound No. | Formula | MP (°C.) MS | Elementary Analysis Calcd Found |
|---|---|---|---|
| 17 | [structure with n-Bu, piperidine, MeO-benzyl, SO2] · 3/2(CO2H)2·1/2H2O MeO | 77–80 MS 605 (M + 1) | C34H44N4O4S·3/2(CO2H)2·1/2H2O<br>C   H     N<br>59.34  6.46  7.48<br>59.57  6.35  7.64 |
| 18 | [structure with Ph, piperidine, MeO-benzyl, SO2] · (CO2H)2·H2O MeO | 92–96 MS 625 (M + 1) | C36H40N4O4S·(CO2H)2·H2O<br>C   H     N<br>62.28  6.05  7.65<br>62.53  6.04  7.49 |
| 19 | [structure with Cl, Me, piperidine, MeO-benzyl, SO2] · (CO2H)2·1/2H2O MeO | 84–89 MS 597 (M + 1) | C31H37N4O4SCl·(CO2H)2·1/2H2O<br>C   H     N<br>56.93  5.79  8.05<br>57.00  5.79  7.95 |
| 20 | [structure with Cl, Me, piperidine, MeO-benzyl, SO2] · (CO2H)2·1/5H2O MeO | 90–95 MS 597 (M + 1) | C31H37N4O4SCl·(CO2H)2·1/5H2O<br>C   H     N<br>57.38  5.75  8.11<br>57.42  5.64  8.11 |

TABLE 1-continued

| Compound No. | Formula | MP (°C); MS | Elementary Analysis Calcd / Found |
|---|---|---|---|
| 21 | [structure with piperidine, phenoxy, sulfonyl, N-Me group, (CO₂H)₂·H₂O AcOCH₂] | 86–89; MS 543 (M + 1) | $C_{27}H_{34}N_4O_6S\cdot(CO_2H)_2\cdot H_2O$<br>C 53.53 / 53.75<br>H 5.89 / 5.75<br>N 8.61 / 8.47 |
| 22 | [structure with piperidine, phenoxy, trans-allyl, sulfonyl, NH, N-Me] | 138–142; MS 455 (M + 1) | $C_{24}H_{30}N_4O_3S$<br>C 63.41 / 63.07<br>H 6.65 / 6.85<br>N 12.32 / 12.28 |
| 23 | [structure with piperidine, phenoxy, allyl, sulfonyl, NH, N-Me] 5/2 H₂O | 116–120; MS 455 (M + 1) | $C_{24}H_{30}N_4O_3S\cdot5/2H_2O$<br>C 57.70 / 57.40<br>H 7.06 / 6.82<br>N 11.21 / 10.85 |
| 24 | [structure with N-methylpiperazine, phenoxy, propyl, sulfonyl, NH, N-Me] HCl·3/2H₂O | 218–223 (dec.); MS 458 (M + 1) | $C_{23}H_{31}N_5O_3S\cdot HCl\cdot3/2H_2O$<br>C 53.02 / 53.12<br>H 6.77 / 6.88<br>N 13.44 / 13.41 |
| 25 | [structure with N-methylpiperazine, phenoxy, cis-allyl, sulfonyl, NH, N-Me] HCl·3H₂O | MS 470 (M + 1) | $C_{24}H_{31}N_5O_3S\cdot HCl\cdot3H_2O$<br>C 51.47 / 51.62<br>H 6.84 / 6.92<br>N 12.50 / 12.47 |

TABLE 1-continued

| Compound No. | Formula | MP (°C.) MS | Elementary Analysis Calcd Found |
|---|---|---|---|
| 26 | (structure with benzamide, piperidine, phenoxy-propyl, sulfonyl guanidine N-Me) · H2O | 80–82 MS 457 (M + 1) | C23H28N4O4S·H2O<br>C 58.21 H 6.37 N 11.81<br>58.14 6.18 11.51 |
| 27 | (structure with CO2Me, piperidine, phenoxy-propyl, sulfonyl guanidine N-Me) · HCl·5/2H2O | 93–97 MS 501 (M + 1) | C25H32N4O5S·HCl·5/2H2O<br>C 51.67 H 6.42 N 9.64<br>51.40 6.34 9.54 |
| 28 | (structure with piperidinylmethyl-phenoxy-butenyl sulfonyl guanidine N-n-Bu) · HCl·1/2H2O | MS 497 (M + 1) | C27H36N4O3S·HCl·1/2H2O<br>C 59.82 H 7.06 N 10.33<br>60.10 7.00 10.34 |
| 29 | (structure with OMe, piperidinylmethyl-phenoxy-butenyl sulfonyl guanidine N-Me) | MS 485 (M + 1) | (Hygroscopic) |

Pharmacological Test 1

Inhibitory activity on gastric acid secretion:

Male Wistar rats (weighing 172 to 200 g) were divided into groups, 7 to 8 rats in each group. The animals were fasted for 24 hours. Under ether anesthesia, the abdomen was incised and the pylorus was ligated according to the method of Shay et al. [Gastroenterology, 1, 420 (1963)]. The animals were sacrificed 4 hours later, and the stomach was removed to collect gastric juice, which was then centrifuged (3000 r.p.m., 10 minutes). The volume of gastric juice and the acidity were measured. The compound to be tested was dissolved in water, and the solution was intraduodenally given to animals at varying doses immediately after the ligation of the pylorus. Tables 2 and 3 show the results.

TABLE 2

| Compound | Dose (mg/kg) | Volume of gastric juice (ml) | Acidity ($\mu$ Eq/ml) | Total acid output ($\mu$ Eq) |
|---|---|---|---|---|
| Control |  | 4.8 ± 1.5 | 78.4 ± 12.0 | 391.6 ± 161.6 |
| Compound 2 | 3 | 3.7 ± 0.9 | 64.8 ± 15.1 | 247.8 ± 96.9 |
|  | 10 | 3.4 ± 1.8 | 54.9 ± 16.1 | 205.9 ± 165.0 |
|  | 30 | 2.4 ± 1.4 | 30.9 ± 16.7 | 85.3 ± 92.7 |

TABLE 3

| Compound | Dose (mg/kg) | Volume of gastric juice (ml) | Acidity ($\mu$ Eq/ml) | Total acid output ($\mu$ Eq) |
|---|---|---|---|---|
| Control |  | 2.5 ± 0.5 | 65.2 ± 10.7 | 162.3 ± 41.6 |
| Compound 22 | 3 | 2.0 ± 0.6 | 8.6 ± 8.2 | 15.5 ± 9.6 |
|  | 10 | 2.3 ± 1.0 | 2.1 ± 3.9 | 4.5 ± 9.4 |
| Compound 28 | 10 | 2.2 ± 0.8 | 59.2 ± 12.4 | 133.3 ± 69.0 |
|  | 30 | 1.5 ± 0.5 | 32.0 ± 14.4 | 53.6 ± 32.9 |
|  | 100 | 1.1 ± 0.5 | 4.9 ± 8.2 | 4.6 ± 7.1 |

Pharmacological Test 2

Effect on hydrochloric acid induced-ulcer:

Male Wistar rats (weighing 156 to 189 g) were divided into groups, 5 to 8 rats in each group. The animals were fasted for 24 hours, and 5 ml/kg of 0.6N hydrochloric acid was given orally. The animals were sacrificed 1 hour later. The stomach was removed, and 1% formalin was injected into the removed stomach to fix the stomach. The stomach was then incised open along the greater curvature. The length (mm) of gastric lesions was measured, summed and used as an ulcer index. The compound to be tested was dissolved in water, and the solution was orally given to animals at varying doses 1 hour before the injection of hydrochloric acid. Tables 5 and 6 show the results.

TABLE 4

| Compound | Dose (mg/kg) | Ulcer index | Percent inhibition (%) |
|---|---|---|---|
| Control |  | 72.7 ± 23.7 |  |
| Compound 2 | 3 | 48.3 ± 17.8 | 33.6 |
|  | 10 | 32.1 ± 24.9 | 55.8 |
|  | 30 | 10.9 ± 17.2 | 85.0 |
|  | 100 | 4.0 ± 6.1 | 94.5 |

TABLE 5

| Compound | Dose (mg/kg) | Ulcer index | Percent inhibition (%) |
|---|---|---|---|
| Control |  | 61.2 ± 25.4 |  |
| Compound 22 | 10 | 51.1 ± 20.4 | 16.5 |
|  | 30 | 39.4 ± 13.2 | 35.6 |
|  | 100 | 31.6 ± 5.0 | 48.4 |

TABLE 6

| Compound | Dose (mg/kg) | Ulcer index | Percent inhibition (%) |
|---|---|---|---|
| Control |  | 150.0 ± 35.2 |  |
| Compound 28 | 10 | 116.1 ± 34.9 | 22.6 |
|  | 30 | 55.8 ± 32.4 | 62.8 |
|  | 100 | 5.1 ± 4.1 | 96.6 |

Pharmacological Test 3

Inhibitory activity on gastric acid secretion was measured in the same manner as in Pharmacological Test 1 with use of Compound 2 below as the present compound and, for comparison, Compound A below of Example 37c in JP-A-116277/1984. Percent inhibition on gastric acid secretion were obtained from the measurements and Table 7 shows the results.

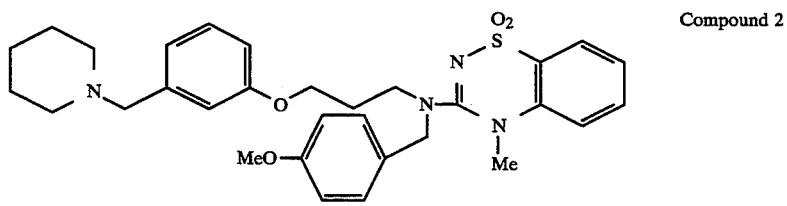

Compound 2

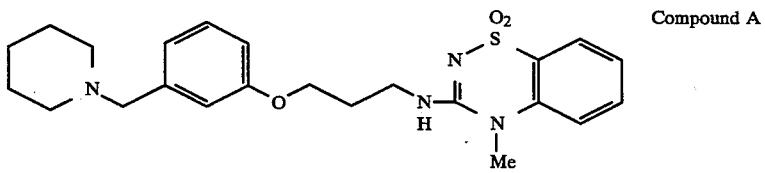

Compound A

TABLE 7

| Compound | Dose (mg/kg) | Percent inhibition (%) |
|---|---|---|
| Compound 2 | 30 | 95.1 |
| Compound A | 30 | 96.2 |

Pharmacological Test 4

Effect on hydrochloric acid induced-ulcer was measured in the same manner as in Pharmacological Test 2 with use of Compound 2 and Compound A. Percent inhibition of effect on hydrochloric acid induced-ulcer were obtained from the measurements and Table 8 shows the results.

TABLE 8

| Compound | Dose (mg/kg) | Percent inhibition (%) |
|---|---|---|
| Compound 2 | 30 | 86.9 |
| Compound A | 30 | 59.4 |

As apparent from the above results, Compound 2 of the present invention is almost equal to Compound A in inhibitory activity on gastric acid secretion, but is extremely excellent than Compound A in effect on hydrochloric acid induced-ulcer. Thus, Compound 2 is well balanced in both activities.

Examples for preparing pharmaceutical compositions with use of the present compound are given below.

Preparation Example 1 (Tablet)

By the usual method, the ingredients in the proportions given below were made into tablets each weighing 300 mg.

| Compound 2 | 100 mg |
|---|---|
| Lactose | 47 mg |
| Corn starch | 50 mg |
| Microcrystalline cellulose | 50 mg |
| Hydroxypropyl cellulose | 15 mg |
| Talc | 2 mg |
| Magnesium stearate | 2 mg |
| Ethyl cellulose | 30 mg |
| Unsaturated fatty acid glyceride | 2 mg |
| Titanium dioxide | 2 mg |

Preparation Example 2 (Granule)

The ingredients in the proportions given below were made into a granular preparation by the usual method in an amount of 1000 mg per wrapper.

| Compound 17 | 200 mg |
|---|---|
| Mannitol | 540 mg |
| Corn starch | 100 mg |
| Microcrystalline cellulose | 100 mg |
| Hydroxypropyl cellulose | 50 mg |
| Talc | 10 mg |

Preparation Example 3 (Fine granule)

The ingredients in the proportions given below were made into a fine granular preparation by the usual method in an amount of 1000 mg per wrapper.

| Compound 22 | 200 mg |
|---|---|
| Mannitol | 520 mg |
| Corn starch | 100 mg |
| Microcrystalline cellulose | 100 mg |
| Hydroxypropyl cellulose | 70 mg |
| Talc | 10 mg |

Preparation Example 4 (Capsule)

By the usual method, the ingredients in the proportions given below were made into an encapsulated preparation in an amount of 250 mg in each capsule.

| Compound 28 | 100 mg |
|---|---|
| Lactose | 50 mg |

-continued

| Corn starch | 47 mg |
|---|---|
| Microcrystalline cellulose | 50 mg |
| Talc | 2 mg |
| Magnesium stearate | 1 mg |

Preparation Example 5 (Syrup)

By the usual method, the ingredients in the proportions given below were made into a syrup preparation in an amount of 100 ml in each phial.

| Compound 2 | 1 g |
|---|---|
| Purified sucrose | 60 g |
| Ethyl p-hydroxybenzoate | 5 mg |
| Butyl p-hydroxybenzoate | 5 mg |
| Flavor | suitable amount |
| Coloring agent | suitable amount |
| Purified water | suitable amount |

Preparation Example 6 (Injection)

The ingredients in the proportions given below were made into an injection by the usual method in an amount of 2 ml per ampoule.

| Compound 17 | 100 mg |
|---|---|
| Distilled water for injections, | suitable amount |

Preparation Example 7 (Suppository)

By the usual method, the ingredients in the proportions given below were made into suppositories each weighing 1500 mg.

| Compound 22 | 100 mg |
|---|---|
| Witepsol S-55 (*a) | 1400 mg |

(*a) a mixture of mono-, di- and tri-glyceride of saturated fatty acids from lauric acid to stearic acid; product of Dynamite Nobel Co., Ltd.

We claim:

1. A benzothiadiazine derivative, a hydrate thereof or an acid addition salt thereof, the derivative being represented by the formula (I)

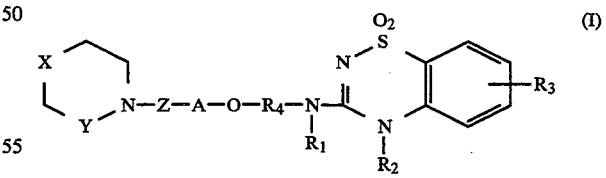

wherein X is methylene or a nitrogen atom substituted with a lower alkyl, Y and Z are each methylene or carbonyl, A is phenylene or phenylene substituted with methoxycarbonyl, $R_4$ is lower alkylene or lower alkenylene, $R_1$ is a hydrogen atom, acetoxyacetyl, cyclohexylmethyl or benzyl wherein the benzene ring may be substituted with lower alkoxyl, halogen atom, nitro, lower alkyl, methylenedioxy or hydroxyl, $R_2$ is lower alkyl or phenyl, and $R_3$ is a hydrogen atom, halogen atom or lower alkoxyl with the exception of the case where X, Y and Z are each methylene, A is unsubstituted phenylene, $R_4$ is lower alkylene and $R_1$ is a hydrogen atom.

2. A benzothiadiazine derivative, hydrate thereof or acid addition salt thereof as defined in claim 1 wherein $R_2$ is methyl or n-butyl.

3. A benzothiadiazine derivative, hydrate thereof or acid addition salt thereof as defined in claim 1 wherein $R_4$ is butenylene and $R_1$ is a hydrogen atom.

4. A benzothiadiazine derivative, hydrate thereof or acid addition salt thereof as defined in claim 1 wherein $R_4$ is trimethylene and $R_1$ is benzyl or benzyl substituted with methoxy.

5. A benzothiadiazine derivative, hydrate thereof or acid addition salt thereof as defined in claim 1 wherein X, Y and Z are each methylene, A is meta-substituted phenylene, $R_4$ is trimethylene, $R_1$ is methoxy-substituted benzyl, $R_2$ is methyl or n-butyl and $R_3$ is a hydrogen atom.

6. A benzothiadiazine derivative, hydrate thereof or acid addition salt thereof as defined in claim 1 wherein X, Y and Z are each methylene, A is meta-substituted phenylene, $R_4$ is cis-butenylene, $R_1$ is a hydrogen atom, $R_2$ is methyl or n-butyl and $R_3$ is a hydrogen atom.

7. A peptic ulcer treating composition comprising an effective amount of the benzothiadiazine derivative, hydrate thereof or acid addition salt thereof as defined in claim 1 and a pharmacological carrier.

8. A method of treating peptic ulcer comprising administering to a patient an effective amount of the benzothiadiazine derivative, hydrate thereof or acid addition salt thereof as defined in claim 1.

* * * * *